United States Patent [19]
Blass et al.

[11] Patent Number: 5,952,357
[45] Date of Patent: Sep. 14, 1999

[54] TREATING DISEASES OF THE ANTERIOR HORN CELLS

[75] Inventors: John Blass, Bronxville; Gary Gibson, Larchmont; Mindy L. Aisen, Scarsdale, all of N.Y.

[73] Assignee: Cornell Research Foundation, Inc., Ithaca, N.Y.

[21] Appl. No.: 08/172,110

[22] Filed: Dec. 23, 1993

[51] Int. Cl.$^6$ .................................................. A61K 31/44
[52] U.S. Cl. ............................................................ 514/352
[58] Field of Search ............................................. 514/352

[56] References Cited

U.S. PATENT DOCUMENTS

| | | | |
|---|---|---|---|
| 4,386,095 | 5/1983 | Gibson et al. | 424/263 |
| 4,508,715 | 4/1985 | Booth et al. | 514/280 |
| 5,171,745 | 12/1992 | De Noble et al. | 514/333 |
| 5,221,683 | 6/1993 | Ulrich et al. | 514/352 |

OTHER PUBLICATIONS

Schmutzler et al., Anaesthesist 33(6), 1984, pp. 294–295.
Bever, C.T., et al, Ann. Neurol, 27, 421–427 (1990).
Bostock, H., et al, J. Physiol., 313, 301–315 (1981).
Kaji, R., et al, Neurology, 38, 1884–1887 (1988).
Lemeignan, M., et al, Brain Res., 304, 166–169 (1984).
Lundh, H., et al, Journal of the Neurol. Sciences, 32, 29–43 (1977).
Lundh, H., Brain Res. 153, 307–318 (1978).
Matsumoto, M., et al, J. Pharmacol. Exp. Ther., 228, 573–578 (1984).
McEvoy, K.M., et al, The New England Journ. of Med., 321, 1567–1571 (1989).
Murray, N.B., et al, Neurology, 31: 265–271 (1981).
Sherratt, R.M., et al, Nature, London, 283, 570–572 (1980).

*Primary Examiner*—Phyllis G. Spivack

[57] ABSTRACT

Administration of aminopyridine, preferably 3,4-diaminopyridine, increases motor strength and Functional Independence Measure in humans afflicted with diseases of the anterior horn cells, e.g., amyotrophic lateral sclerosis.

9 Claims, 3 Drawing Sheets

TREATING DISEASES OF THE ANTERIOR HORN CELLS

TECHNICAL FIELD

This invention is directed to treating a human with a disease of the anterior horn cells, to increase motor strength in said human.

BACKGROUND OF THE INVENTION

Diseases of the anterior horn cells are characterized by death of motor neurons resulting in prolonged and sometimes permanent and progressive motor weakness. The conventional therapy for the motor weakness is rehabilitation therapy, i.e., physical and/or occupational therapy.

SUMMARY OF THE INVENTION

It has been discovered herein that administration of aminopyridine compound, preferably 3,4-diaminopyridine, to a human affected with a disease of the anterior horn cells causes increased motor strength in the affected human.

In short, the present invention is directed to a method for treating a human with a disease of the anterior horn cells, said method comprising the step of administering aminopyridine having the formula

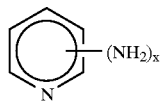

wherein x is 1 or 2 (hereinafter sometimes referred to as "an aminopyridine compound herein" or as "the aminopyridine compounds herein"), to said human in a therapeutically effective amount, thereby to increase motor strength in said human. It is preferably used as an adjunct to rehabilitative therapy, i.e., physical and/or occupational therapy, to enhance the therapeutic benefit (i.e., the motor strength improving benefit) thereof. The experimental work herein was carried out on those with amyotrophic lateral sclerosis; however, the invention has application to all diseases of the anterior horn cells. Preferred dosages range from 30 to 100 mg per day.

The phrase "cause increased motor strength" is used herein to mean increased motor strength within one hour of administration of an aminopyridine compound herein compared to motor strength prior to administration of said aminopyridine compound.

DETAILED DESCRIPTION

Figure 1:
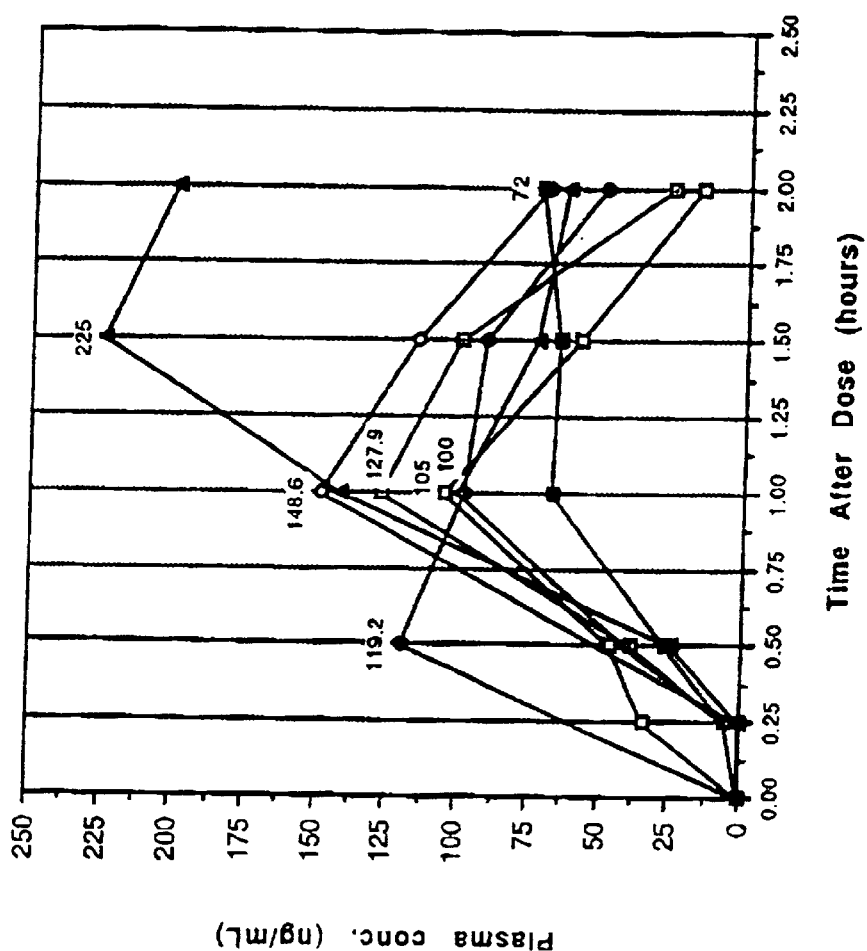
FIG. 1 depicts graphs of plasma concentration of 3,4-diaminopyridine versus time after dose for 7 patients and shows results of Example I.

The invention herein applies to all diseases of the anterior horn cells. These include infectious diseases, e.g., acute infectious poliomyelitis (illness characterized by viral invasion of the central nervous system, resulting in disseminated death of motor neurons, producing motor weakness and paralysis, caused, for example by infection by any of three types of poliovirus, other enteroviruses such as Coxsackieviruses A and B and echo picorna viruses), post polio syndrome (a chronic condition that occurs in polio survivors after a substantial time has elapsed since the acute phase of the illness, characterized by progressive weakness and functional disability developing in an individual with previously static deficits, and Creutzfeld-Jacob Syndrome; nutritional and toxic disorders, e.g., Combined System Disease (a syndrome which includes damage to upper and lower motor neurons, caused by vitamin $B_{12}$ deficiency), and degeneration of motor neurons after exposure to aluminum, vincristine or acetyl ethyl tetramethyl tetralin; structural disorders, e.g., mass occupying lesions of the spinal cord indirectly impinging on motor neurons, causing dysfunction and cell death, including, e.g., syringomyelia (cyst), malignant metastatic tumors, primary spinal cord tumors (ependymoma, glioma), and vascular malformations; traumatic injuries, e.g., acute cervical spinal cord injury associated with delayed progressive "drop-out" of post-synaptic anterior horn cells in thoracic and lumbar cord; and degenerative diseases, e.g., amyotrophic lateral sclerosis (also referred to as ALS), progressive bulbar palsy, progressive muscular atrophy, primary lateral sclerosis, presenile dementia with motor neuron disease, spinal muscular atrophies, olivopontocerebellar atrophy, Joseph disease, Parkinson's disease, Huntington's chorea and Pick's disease.

Aminopyridine compounds having the above structural formula wherein x is 1 are 2-aminopyridine, 3-aminopyridine and 4-aminopyridine. Aminopyridine compounds having the above structural formula wherein x is 2 are 2,3-diaminopyridine; 2,5-diaminopyridine; 2,6-diaminopyridine; 3,4-diaminopyridine; 4,5-diaminopyridine and 4,6-diaminopyridine. Citations to the preparation of 2-aminopyridine and 3-aminopyridine are found in the Merck Index, 11th edition at page 488. The compound 4-aminopyridine is a known compound. See for example, Booth et al U.S. Pat. No. 4,508,715; Bostock, H., et al, J. Physiol., 313:301–315 (1981); and Lundh, H., Brain Res., 153:307–318 (1978). The compound 3,4-diaminopyridine is commercially available, e.g., from Regis Chemical Corporation, Morton Grove, Ill. The syntheses of the others of the aminopyridine compounds herein are considered obvious.

The aminopyridine compounds herein are readily formulated for administration in solid dosage form together with conventional carriers and excipients, e.g., starch, lactose, cellulose derivatives, magnesium stearate, stearic acid, and the like or in liquid dosage form, e.g., together with injectable liquid, e.g., water or isotonic saline. The aminopyridine compounds herein are readily administered orally or parenterally (e.g., intravenously).

A therapeutically effective amount of aminopyridine compound herein, i.e., an amount which increases motor strength, generally ranges from 5 mg to 100 mg per day. Maximum tolerated dosage within this range can be readily established by starting with a low amount in said range and increasing dosage daily until 100 mg is reached or a lesser limit is determined by development of laboratory abnormalities or level of side effect(s) unacceptable to the patient. For example, a maximum tolerated dosage for 3,4-diaminopyridine can be established by starting with 20 mg for the first day and increasing by 10 mg per day to obtain a maximum tolerated dosage as determined by complaint by the patient of a level of abdominal cramping unacceptable to the patient, of no more than 100 mg per day. Typically, a maximum tolerated dosage of aminopyridine compound herein ranges from 30 mg to 100 mg per day. The therapeutically effective amount is preferably the maximum tolerated dosage administered either as a single dose, or for extended effect, divided into multiple doses administered no more often than at intervals of 1–3 hours, e.g. divided into four doses administered at intervals of three hours during waking hours. Serum level monitoring is appropriately utilized to develop dosages and dosage intervals after a first administration of the maximum tolerated dosage consistent with not exceeding the peak serum level obtained after administration of the maximum tolerated dosage.

Preferably, the treatment with aminopyridine compound herein is carried out as an adjunct to rehabilitation therapy on motor weakness, i.e., physical and/or occupational therapy, e.g., carried out on a daily basis, e.g., five days a week. The two treatments (aminopyridine administration and rehabilitation therapy) are considered to reinforce each other, i.e., the treatment with the aminopyridine causes the rehabilitation therapy to be more successful.

The invention is illustrated in the following example.

EXAMPLE

Treatment was carried out on seven amyotrophic lateral sclerosis (ALS) patients (4 male, 3 female, ages 48–68, 1.7–4.8 years since diagnosis) with disabling motor weakness who were admitted to the Burke Rehabilitation Hospital, White Plains, N.Y. Assessment on admission included CBC, renal and liver function tests, EKG and EEG; any significant laboratory abnormality precluded study participation.

Patients received a single daily oral dose of 3,4-diaminopyridine. The Burke Rehabilitation Hospital Pharmacy compounded the dosage formulation, combining 10 mg 3,4-diaminopyridine with 250 mg lactose in a clear gelatin capsule. The maximum tolerated dosage of 3,4-diaminopyridine for each patient was established as described above, starting with 20 mg and increasing the dosage 10 mg each succeeding day stopping at the lesser of the level determined by complaint by the patient of a level of abdominal cramping unacceptable to the patient or 100 mg.

Each of the patients was also administered rehabilitation therapy (individualized physical and/or occupational therapy) daily, Monday through Friday).

The maximum tolerated dosage of 3,4-diaminopyridine established for Patient A was 60 mg; the maximum tolerated dosage established for Patient B was 80 mg; the maximum tolerated dosage established for Patient C was 30 mg; the maximum tolerated dosage established for Patient D was 80 mg; the maximum tolerated dosage established for Patient E was 100 mg; the maximum tolerated dosage established for Patient F was 100 mg; and the maximum tolerated dosage established for Patient G was 70 mg.

Plasma concentrations of 3,4-diaminopyridine were determined on each patient 15 minutes, 30 minutes, 60 minutes, 90 minutes and 120 minutes after administration of the maximum tolerated dosage. Plasma concentration of 3,4-diaminopyridine results including peak serum levels are shown in FIG. 1 wherein "conc." stands for concentration. In FIG. 1, the results for Patient A are denoted by the graph defined by open boxes with a dot therein (peak level of 3,4-diaminopyridine of 127.9 ng/ml at 1 hour after administration); the results for Patient B are denoted by the graph defined by open circles (peak level of 3,4-diaminopyridine of 148.6 ng/ml at 1 hour after administration); the results for Patient C are denoted by the graph defined by open squares with no dot therein (peak level of 3,4-diaminopyridine of 105 ng/ml at 1 hour after administration); the results for Patient D are denoted by the graph defined by filled in circles (peak level of 3,4-diaminopyridine of 119.2 ng/ml at 30 minutes after administration); the results for Patient E are denoted by the graph defined by filled in squares (peak level of 3,4-diaminopyridine of 72 ng/ml at 2 hours after administration); the results for Patient F are denoted by the graph defined by filled in triangles with a white dot therein (peak level of 3,4-diaminopyridine of 100 ng/ml at 1 hour after administration); and the results for Patient G are denoted by the graph defined by filled in triangles without a white dot therein (peak level of 3,4-diaminopyridine of 225 ng/ml 90 minutes after administration). The mean peak serum level of 3,4-diaminopyridine was $128 \pm 50$ ng/ml, occurring $1.14 \pm 0.50$ hours after administration. Concentrations of 3,4-diaminopyridine peaked in four patients one hour after administration with an approximate half-life of 2 hours.

Evaluations were carried out on patients prior to their receiving any 3,4-diaminopyridine (pre-DAP), one hour after their receiving maximum tolerated dosage of 3,4-diaminopyridine (on-DAP), 4–10 days after discontinuing 3,4-diaminopyridine (post-DAP) and in the case of evaluation of functional performance also by telephone followup 3 to 6 months after discharge.

Statistical analysis was performed with the Statview II statistical software program on a Macintosh II computer. One factor analysis of variance (ANOVA) and post hoc analysis was used to examine the relationships between pre, on and post DAP phases, and FIM, motor, nerve conduction and neuropsychological testing performance.

Figure 2:
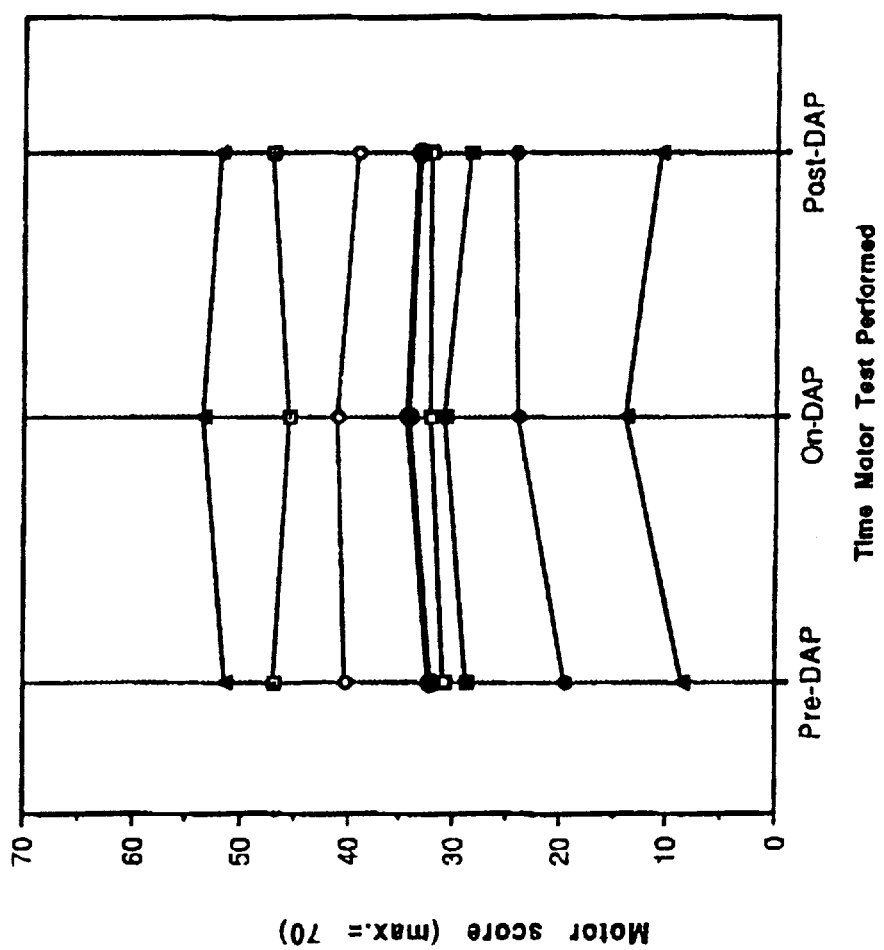
FIG. 2 depicts graphs of motor score versus time of motor test performance, for 7 patients, and for mean values, and shows results of Example I.

For motor evaluations, motor examinations conducted by a physical therapist were videotaped. Two neurologists independently reviewed these tapes while "blinded" as to which tapes were of patients on drug. Fourteen muscle group functions were scored from "0" to "5" as follows: 0=no contraction; 1=trace contraction; 2=active movement possible with gravity eliminated; 3=antigravity strength; 4=reduced function, but adequate to overcome some resistance; and 5=normal strength. The motor score was the sum of the muscle group scores; a maximum score of 70 could therefore be generated in a normal healthy individual. The quantitative assessments generated by each neurologist were consistent between neurologists (correlation=0.986). The assessments of the neurologists were averaged. The averaged results for each patient and for mean scores are set forth in FIG. 2 wherein "max." means maximum, and "Pre-DAP", "On-DAP" and "Post-DAP" have meanings as described above. In FIG. 2, the thicker graph defined by the bigger filled in circles denotes the mean values, the top graph defined by filled in triangles provides the results for Patient G: the next graph, defined by the open squares with a dot therein, provides the results for Patient A; the next graph, defined by open circles, provides the results for Patient B: the first graph under the graph for means, i.e., the graph defined by open squares without dots therein, denotes results for Patient C; the next graph, i.e., the one defined by filled in squares denotes results for Patient E; the next graph, i.e., the one defined by filled in circles (smaller than those defining the mean values graph), denotes results for Patient D; and the lowest graph, i.e., the one defined by filled in triangles with white dots therein, denotes results for Patient F. As shown in FIG. 2, a modest peak in averaged motor score occurred on drug. One factor ANOVA and post hoc analysis showed a statistically significant ($F(6,13)=6.39$, $p=0.045$) difference between baseline and on-DAP motor scores. Although a decline in motor performance was seen when 3,4-diaminopyridine was discontinued, it did not reach statistical significance ($F(6,13)=2.76$, $p=0.148$).

Figure 3:
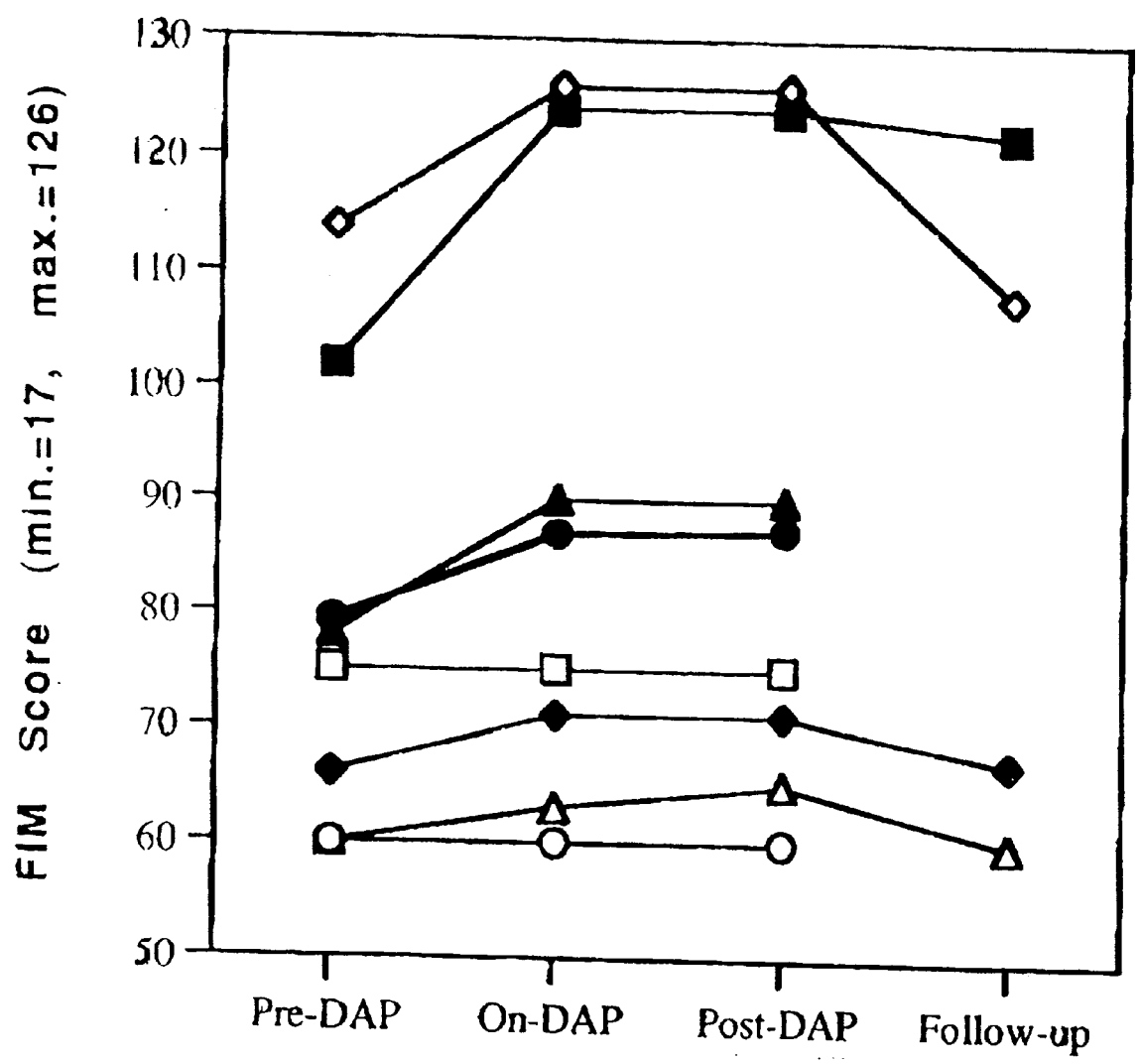
FIG. 3 depicts graphs of Functional Independence Measure (FIM) score versus time of FIM test performance, for 7 patients, and for mean values, and shows results of Example I.

To assess the effect of 3,4-diaminopyridine on functional performance, a Functional Independence Measure (FIM) score was generated by a certified occupational therapist for each patient prior to drug administration (i.e., pre-DAP), one hour after drug (maximum tolerated dosage) administration (i.e. on-DAP), 4–10 days after drug administration (post-DAP), and by telephone follow-up 3 to 6 months after discharge (follow-up). The FIM is a widely used and validated descriptive functional scoring system, developed for use in rehabilitation centers (Granger, C. V., Hamilton, B. B., Sherwin, F. S., Guide for the use of the uniform data set for medical rehabilitation, Uniform Data System for Medical Rehabilitation Project Office, Buffalo General Hospital, Buffalo, N.Y., 1986). A minimum score of 17 and a maximum score of 126 could be generated. Results are set forth in FIG. 3 wherein "Pre-DAP", "On-DAP", "Post-DAP", and "Follow-up" have the same meaning as described above, "min." means minimum and "max." means maximum. In FIG. 3, the graph defined by the filled in circles denotes the mean values; the graph defined by the filled in squares provides the results for Patient A; the graph defined by the filled in triangles provides the results for Patient B; the graph defined by filled in diamonds provides results for Patient C; the graph defined by open circles provides results for Patient D: the graph defined by open squares provides results for Patient E; the graph defined by open triangles provides results for Patient F; and the graph defined by open diamonds provides results for Patient G. A statistically significant ($F(6,13)=6.42$, $p=0.045$) improvement in F performance was apparent between baseline and on-DAP assessments. However, as shown in FIG. 3, The FIM scores did not change when the drug administration was discontinued. They remained stable through discharge shortly thereafter. Follow-up FIM scores (obtained 3–6 months after discharge in four patients) did show a decline in performance but generally remained higher than baseline FIM scores, and did not show significant difference from on-DAP or post-DAP assessments ($F(3,7)=0.44$, $p=0.553$).

Nerve conduction, a standard electrophysiological clinical method, was performed on median and ulnar nerves. Modest increases in evoked response amplitudes and conduction velocities were seen with patients on 3,4-diaminopyridine, but this did not reach statistical significance. No changes in conduction block when present, or F-responses were seen.

As indicated above, dosage for Patients A, B, C, D and G was limited by complaints of abdominal cramping.

Side effects for the patients on maximum tolerated dosages were as follows: Patient A, perioral tingling; Patient B, mild abdominal cramping; Patient C, minimal perioral tingling; Patient D, abdominal cramping, perioral tingling, anxiety; Patient E, abdominal cramping; Patient F, perioral tingling; and Patient G, perioral tingling. In no case did laboratory abnormalities develop.

Cognitive and affective examinations were conducted pre-DAP, on-DAP and post-DAP as follows: The Hamilton Depression Rating Scale (Hamilton, M, J. Neurol. Neurosurg. Psychiatry, 23, 56–62, 1960), hereinafter referred to as Ham-D, was administered to five patients; in one patient, severe dysarthria interfered with the Ham-D, and the self-tested Zung depression scale (Zung, W. W. K., Arch. Gen. Psychiatry, 12:63–70, 1965) was substituted. The Mini Mental State Examination (Folstein, M. F., et al, J. Psychiatry Res 12, 189–198, 1975), hereinafter MMSE, was given to six patients. One patient could not participate in neuropsychological testing due to inadequate English comprehension. No statistically significant effect of 3,4-diaminopyridine on affect was apparent. Although those who received the Ham-D showed the lowest ratings during the drug phase (mean score=4.5±3.4), this was not significantly different from either baseline (8.5±8.8; $p=0.43$) or wash-out phase (5.3±3.4; $p=0.69$). The patient who received the Zung scale had equivalent scores on and off 3,4-diaminopyridine. Three of the six patients given the MMSE were unable to perform tasks requiring motor skills, and their test scores were prorated. No significant differences in mean MMSE scores occurred across treatment conditions (pre-DAP: 27.6±2.3), on-DAP: 27.2±2.0), post-DAP: 26.5±2.5, pre vs. on: $p=0.34$, on vs. post: $p=0.48$.

It is expected that similar results to those achieved in Example I are obtained on administration of 3,4-diaminopyridine in dosages established the same way as in Example I when the patients are afflicted with any of the anterior horn cell diseases listed herein, e.g., post-polio syndrome.

Similar results to those achieved in Example I are obtained on administration of 4-aminopyridine in dosages established the same way as in Example I for 3,4-diaminopyridine.

Many variations of the above will be obvious to those skilled in the art. Thus, the invention is defined by the claims.

What is claimed is:

1. A method of treating a human having a disease of the anterior horn cells, said method comprising administering an aminopyridine having the formula

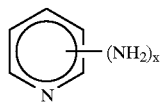

wherein x is 1 or 2, to said human in a therapeutically effective amount, thereby to increase motor strength in said human.

2. The method of treating a human having a disease of the anterior horn cells as recited in claim 1 wherein the aminopyridine is 3,4-diaminopyridine.

3. The method of treating a human having a disease of the anterior horn cells as recited in claim 1 wherein the disease is amyotrophic lateral sclerosis.

4. The method of claim 3 wherein the aminopyridine is 3,4-diaminopyridine.

5. The method of treating a human having a disease of the anterior horn cells as recited in claim 1 wherein the therapeutically effective amount ranges from about 5 to 100 mg per day.

6. The method of treating a human having a disease of the anterior horn cells as recited in claim 5 wherein the therapeutically effective amount ranges from about 30 to 100 mg per day.

7. The method of treating a human having a disease of the anterior horn cells as recited in claim 5 wherein said human is also treated with rehabilitation therapy.

8. The method of claim 1 wherein the aminopyridine has the depicted formula wherein x is 2.

9. The method of claim 8 wherein said disease is amyotrophic lateral sclerosis.

* * * * *